United States Patent [19]

Gray et al.

[11] 4,261,651
[45] Apr. 14, 1981

[54] LIQUID CRYSTAL COMPOUNDS

[75] Inventors: George W. Gray, Cottingham; Damien G. McDonnell, Malvern, both of England

[73] Assignee: The Secretary of State for Defence in her Britannic Majesty's Government of the United Kingdom of Great Britain and Northern Ireland, London, England

[21] Appl. No.: 41,889

[22] Filed: May 23, 1979

[30] Foreign Application Priority Data

May 31, 1978 [GB] United Kingdom ............... 25551/78

[51] Int. Cl.³ .................. C07C 121/60; C07C 121/75; C09K 3/34; G02F 1/13
[52] U.S. Cl. .................................. 350/350 R; 73/356; 252/299; 260/465 F; 260/465 R
[58] Field of Search ........................ 260/465 F, 465 R; 350/350 R; 252/299

[56] References Cited

U.S. PATENT DOCUMENTS

| 4,035,056 | 7/1977 | Coates et al. ............... 260/465 F X |
| 4,113,647 | 9/1978 | Coates et al. ........................ 252/299 |

Primary Examiner—Dolph H. Torrence

Attorney, Agent, or Firm—Stevens, Davis, Miller & Mosher

[57] ABSTRACT

A liquid crystal compound having the formula:

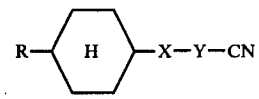

where
X is —$CH_2.CH_2$— or $CH_2O$
Y is

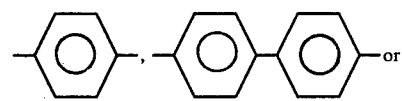

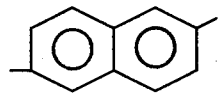

and
R is a straight or branched (possibly chiral) alkyl group having up to 15 carbon atoms.

30 Claims, No Drawings

LIQUID CRYSTAL COMPOUNDS

The present invention is concerned with novel cyclohexane containing derivatives of benzonitrile, 2-cyanonaphthalene, and 4-cyanobiphenyl that possess liquid crystal properties.

Liquid crystal phases are exhibited by certain organic compounds and constitute an intermediate phase that exists between the crystalline solid and the fully disordered liquid phase and within which certain long range ordering of the molecules takes place.

There are two broad types of liquid crystal phase; the smectic mesophase in which the long range ordering is of a substantially lamellar type and the nematic mesophase in which the ordering is substantially linear, ie the molecules tend to line up with the long axes of the molecules parallel. Included sometimes as a sub-class of the nematic phase and sometimes as a separate mesophase is the cholesteric mesophase. This last type has a helical long-range order superimposed upon the linear order of the nematic mesophase.

In accordance with the present invention liquid crystal compounds with a high positive dielectric anisotropy are provided having a general formula:

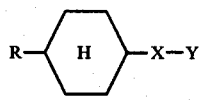

where R is an alkyl group containing up to 15 carbon atoms, and preferably three to nine carbon atoms, which may be normal or branched and which may include a chiral centre; X is —CH$_2$CH$_2$—, or —CH$_2$O—; and Y is

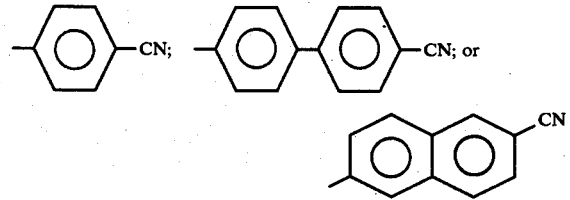

The high positive dielectric anisotropy displayed by the compounds of the present invention make them particularly suitable for use in electro-optic display devices and in accordance with an aspect of the present invention an electro-optic display device of the twisted nematic type or of the phase-change type includes as its liquid crystal material a mixture of two or more of the liquid crystal compounds of the present invention or mixtures (solutions) of one or more such compounds with other liquid crystal materials.

Advantageously an electro-optic display device of the twisted nematic type incorporates as its liquid crystal material at least one compound of the present invention in conjunction with one or more alkyl- or alkyloxy-cyanobiphenyls or alkyl- or alkyloxy-cyanoterphenyls and furthermore advantageously an electro-optic device of the phase change type includes as its liquid crystal material a mixture as defined immediately above, save that the compound of the present invention includes a chiral centre.

In accordance with a further aspect of the present invention a compound of the present invention includes a chiral centre such that the compound when on its own or mixed with other liquid crystal materials when in a thin film in the Grandjean plane texture rotates the plane of polarisation of incident polarised light and reflects elliptically polarised light of specific wavelengths when illuminated by ordinary light so that the mesophases are thermochromic. This occurs, it is believed, because the helical pitch lengths of the molecular formations are such as to give strongly temperature dependent Bragg reflection of particular wavelengths of light in the visible spectral region. That is, the materials appear coloured with a colour which varies with the temperature of the material, and mixtures thereof may thus be used in surface thermography, eg for the detection of breast cancer. This last mentioned property may also be used to produce a temperature sensitive display device eg a thermometer, giving a visual display resulting from the effect of temperature on the helical pitch of the material.

The present invention will now be described, by way of example only, with reference to the following Examples, which illustrate methods of preparation of compounds of the present invention and give the properties of certain members.

In the following description of this specification the following symbols have the meanings ascribed to them below:

C indicates the crystal phase,
S$_A$ indicates the smectic A mesophase
S$_E$ indicates the smectic E mesophase,
S$_B$ indicates the smectic B mesophase,
Ch indicates the cholesteric mesophase,
Phase transitions are indicated thus
C—S$_A$— crystal to smectic A
( ) brackets around a temperature indicate a monotropic transition not observed during a heating cycle,
ΔH is the total enthalpy of fusion for the change from stable crystal phase C to S$_A$ or a liquid crystal phase,
(+) which refers to optically active materials having a positive optical rotary power,
(−) which refers to optically active materials having a negative rotary power,
[α]$_D^{20}$ which is an absolute measure of the rotary power (the specific rotation of an optically active material when forming a 10% w/w solution in chloroform).

The compounds of the present invention are described as follows:

EXAMPLE 1

This example describes the preparation of 4-[trans-4″-n-alkylcyclohexyl methoxy]-4′-cyanobiphenyls by the following route:

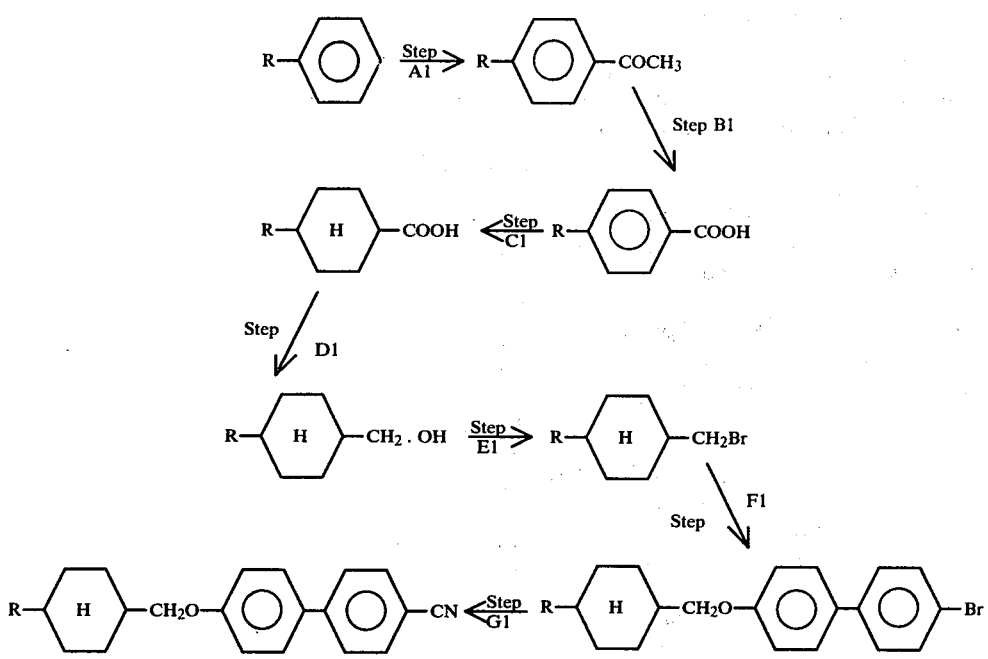

where R is a normal alkyl group.

The synthetic steps, where R=n-propyl, will now be described by way of example.

Step A1: The production of 4-n-propylacetophenone

Crushed anhydrous aluminium trichloride (1.28 mole) was suspended in dry carbon disulphide (348 ml). Acetylchloride (1.1 mole) and n-propylbenzene (1.0 mole) was dissolved in dry carbon disulphide (348 ml) and added to the suspension of aluminium trichloride under anhydrous conditions. The mixture was then left to stir overnight. The solvent was distilled from the reaction mixture and the viscous residue poured onto crushed ice and stirred for 0.5 hours. The product was extracted into ether and the extract washed with water and dried ($Na_2SO_4$). The ether was removed by distillation and the oily residue distilled. The product had mpt 132° C. at 0.1 mm Hg.

Step B1: The production of 4-n-propylbenzoic acid

A solution of sodium hypobromite prepared by dissolving bromine (1.0 mole) in a solution of sodium hydroxide (3.5 mole) in water (700 ml) at 0° C. was added to a well stirred solution of 4-n-propylacetophenone (0.2 mole), prepared in step A1, in dioxan (500 ml). Throughout the addition and for 0.25 hours afterwards the temperature was maintained at 35°–45° C. The excess of sodium hypobromite wad destroyed by adding a solution of sodium metabisulphite. Water (3.5 L) was added and bromoform distilled from the reation mixture. On cooling, the solution was acidified with concentrated hydrochloric acid and the precipitated product filtered off and washed with water. The product was crystallised from ethanol/water to yield white crystals mpt 141.2° C.

Step C1: The production of trans-4-n-propylcyclohexane-1-carboxylic acid

A solution of 4-n-propylbenzoic acid (0.2 mole) in sodium hydroxide (0.205 mole) dissolved in water (160 ml) was hydrogenated in the presence of Raney nickel catalyst (10 g) in an autoclave (1 L) at 195° C. and at a pressure of hydrogen of 170 atm for 30 hours. On cooling, the catalyst was filtered off and the filtrate washed with ether. The aqueous layer was separated and acidified. The precipitated acids were extracted into ether and the ether extracts washed with water and then dried ($Na_2SO_4$). The ether was distilled off and the acids dissolved in methanol (200 ml). The solution was treated successively with 40 g and 30 g of thiourea. After each treatment with thiourea the crystalline material formed was filtered off. The combined crystallisates were dissolved in a 5% solution (800 ml) of potassium hydroxide in water. This solution was acidified and the trans-4-n-propylcyclohexane-1-carboxylic acid precipitated was extracted into ether. The ether extract was washed with water and dried ($Na_2SO_4$). The ether was evaporated off and the product was crystallised from acetone, and had mpt 99° C.

Step D1: The production of trans-4-n-propylcyclohexylmethanol

Trans-4-n-propylcyclohexane-1-carboxylic acid (0.14 mole) was dissolved in sodium dried ether (150 ml) and added dropwise to a vigorously stirred suspension of lithium aluminium hydride (0.3 mole) in sodium dried ether (300 ml). When addition was completed the mixture was heated under reflux for 2 hours. On cooling, water was cautiously added to destroy the excess of lithium aluminium hydride. The mixture was then poured into a 20% hydrochloric acid solution and stirred until the inorganic salts were dissolved. The product was extracted into ether, which was then washed with water and dried ($MgSO_4$). The ether was evaporated off and the residue distilled. The product boils at 148° C. at a pressure of 25 mm Hg.

Step E1: The production of trans-4-n-propylcyclohexylmethyl bromide

Trans-4-n-propylcyclohexylmethanol (0.12 mole) was added to red phosphorus (0.03 g atom) and warmed gently (ca 30° C.) using an oil bath. Bromine (0.14 mole) was added dropwise to the mixture. When addition was complete (about ½ hour) the temperature of the oil bath was raised to 180° C. for one hour. After this time, the mixture was allowed to cool, shaken with ether and filtered. The filtrate was washed with water, then dried ($Na_2SO_4$). The ether was removed by distillation and the residue distilled. The product boiled at 112° C. at a pressure of 15 mm Hg.

Step F1: The production of 4-[trans-4″-n-propylcyclohexylmethoxy]-4′-bromobiphenyl Commercially available 4-benzenesulphonyloxy-4′-bromobiphenyl (0.02 mole) was heated under reflux for two hours with sodium hydroxide (0.05 mole), water (48 ml) and dioxan (96 ml). Trans-4-n-propylcyclohexylmethyl bromide (0.02 mole) was then added and the mixture heated for a further 20 hours under reflux. On cooling, the mixture was poured into water (500 ml) and the precipitated product extracted into chloroform. The combined chloroform extracts were washed with water and dried ($Na_2SO_4$). The chloroform was removed by distillation and the residue crystallised from ethanol to a constant melting point of 154° C. and a nematic to isotropic liquid transition temperature of 176° C.

Step G1: The production of 4-[trans-4″-n-propylcyclohexylmethoxy]-4′-cyanobiphenyl A solution of 4-[trans-4″-n-propylcyclohexylmethoxy]-4′-bromobiphenyl (0.013 mole) in N-methylpyrrolidone (15 ml) was heated under reflux and vigorously stirred with cuprous cyanide (0.018 mole) for 1.5 hours. On cooling, the reaction mixture was poured into a solution of:

Iron (III) Chloride (0.027 mole)
Concentrated hydrochloric acid (1.0 ml)
Water (50 ml)

and stirred at 50° C. for 0.5 hours.

The product was extracted into ether and the combined extracts were washed with water and dried ($Na_2SO_4$). The ether was removed by distillation and the crude product purified by column chromatography (silica gel column eluted with chloroform) and crystallisation from hexane.

Physical constants for this compound and others similarly prepared are given in Table 1 below.

TABLE 1

R—⟨H⟩—$CH_2O$—⟨○⟩—⟨○⟩—CN

| R | C—$S_A$/N (°C.) | $S_A$—N (°C.) | N—I (°C.) | ΔH k cal mol$^{-1}$ |
|---|---|---|---|---|
| n-$C_3H_7$ | 124 | — | 198.8 | 4.8 |
| n-$C_4H_9$ | 93 | — | 193 | 7.5 |
| n-$C_5H_{11}$ | 107 | 136.3 | 193.2 | 4.8 |
| n-$C_6H_{13}$ | 107.3 | 161.8 | 185.7 | 5.2 |
| n-$C_7H_{15}$ | 107.4 | 171.5 | 183.6 | 6.6 |
| n-$C_8H_{17}$ | 96 | 173.7 | 177.2 | 4.9 |

EXAMPLE 2

This examples describes the preparation of (+)-4-[trans-4″-alkylcyclohexylmethoxy]-4′-cyanobiphenyls by the following route:

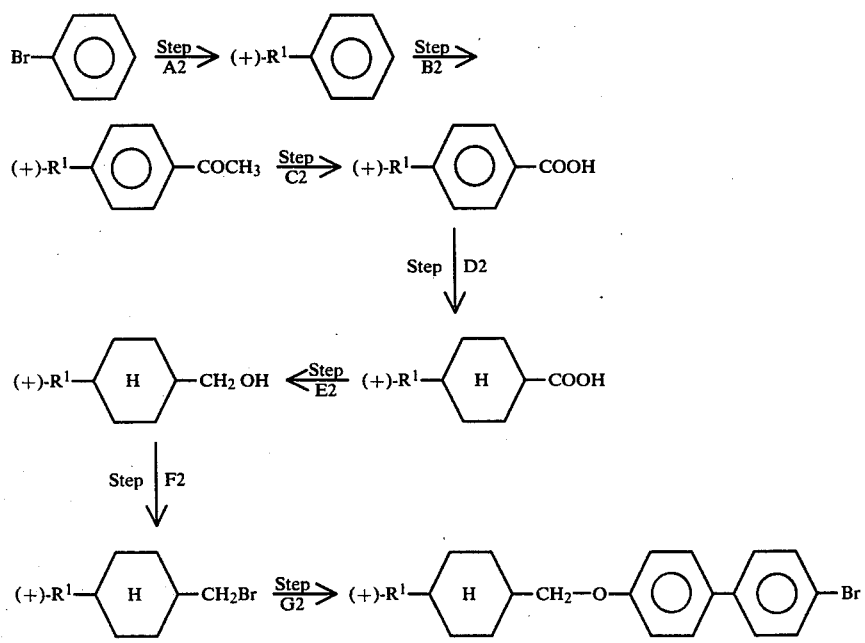

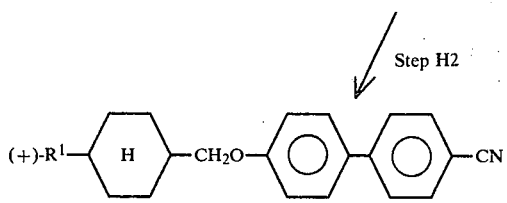

where R[1] is a branched, chiral alkyl group.

The synthetic steps, where R is the (+)-2-methylbutyl group, will now be described by way of example.

Step A2: The production of (+)-2-methylbutylbenzene

A solution of bromobenzene (0.51 mole) in sodium dried ether (200 ml) was added in drops to magnesium turnings (0.51 g atom) in sodium dried ether (50 ml). A single crystal of iodine was added to initiate the reaction, which was kept going by the addition of the bromobenzene. When addition was complete the solution was heated under reflux for 1 hour.

The solution of the Grignard reagent was then cooled in an ice bath and anhydrous iron (III) chloride (0.005 mole) in ether (2 ml) added. A solution of (+)-2-methylbromide (0.54 mole) in sodium dried ether (100 ml) was then added during 30 minutes. The mixture was left to stir for 48 hours at 25° C. The mixture was then poured into a 20% solution of hydrochloric acid in water (300 ml), cooled to 0° C. and stirred for ½ hour. The product was extracted into ether and the combined extracts were washed with water and dried ($Na_2SO_4$). The ether was removed by distillation and the oily residue distilled. The fraction of (+)-2-methylbutylbenzene boiling at 120° C. was collected under partial water pump vacuum (30 mm Hg).

Step B2: The production of (+)-4-(2'-methylbutyl)acetophenone

This was prepared in an analogous manner to that described in Step A1 of Example 1. The product had bpt 100° C. at 0.5 mm Hg.

Step C2: The production of (+)-4-(2'-methylbutyl)benzoic acid

This was prepared in an analogous manner to that described in Step B1 of Example 1. The product had mpt 130° C.

Step D2: The production of (+)-trans-4-(2'-methylbutyl)cyclohexane-1-carboxylic acid This was prepared in an analogous manner to that described in Step C1 of Example 1. The product had mpt 50.5° C.

Step E2: The production of (+)-trans-4-(2'-methylbutyl)cyclohexylmethanol

This was prepared in an analogous manner to Step D1 of Example 1.

The product had bpt 164° C. at a pressure of 25 mm Hg.

Step F2: The production of (+)-trans-4-(2'-methylbutyl)cyclohexylmethyl bromide This was prepared in an analogous manner to Step E1 of Example 1.

The product had bpt 170° C. at a pressure of 20 mm Hg.

Step G2: The production of (+)-4-[trans-4''-(2'''-methylbutyl)cyclohexylmethoxy]-4'-bromobiphenyl This was prepared in an analogous manner to Step F1 of Example 1.

The product had the constants: $C-S_E$, 99° C.; $S_E-S_B$, 135° C.; $S_B-S_A$, 137° C.; $S_A-I$, 166° C.

Step H2: The production of (+)-4-[trans-4''-(2'''-methylbutyl)cyclohexylmethoxy]-4'-cyanobiphenyl This was prepared in an analogous manner to Step G1 of Example 1.

The product had the constants: $C-S_A$, 120° C.; $S_A-Ch$, 144° C.; $Ch-I$, 157.5° C.

Pitch length of a 10% w/w solution in 4-n-pentyl-4'-cyanobiphenyl is 4.6 μm.

EXAMPLE 3

This example describes the preparation of 1-[trans-4'-alkylcyclohexyl)]-2-{4''-[4'''-cyanobiphenylyl]}ethanes by the following route:

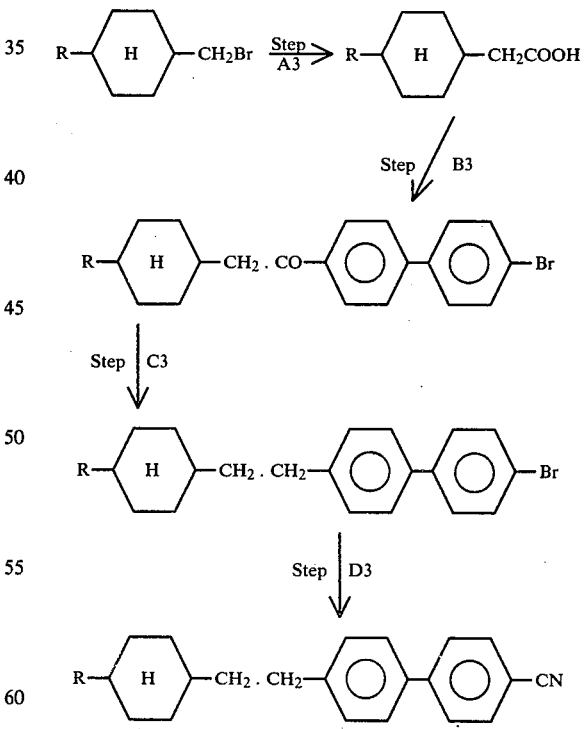

where R is a normal or branched alkyl group, which may be chiral.

The synthetic steps, where R=n-propyl, will now be described by way of example.

Step A3: The production of trans-4-n-propylcyclohexylacetic acid trans-4-n-Propylcyclohexylmethyl bromide (0.08 mole), prepared in Step E1 of Example 1, was converted to the corresponding Grignard reagent by a method analogous to that employed for phenyl magnesium bromide in Step A2 of Example 2.

The solution of Grignard reagent was poured onto a mixture of ether (300 ml) and crushed solid carbon dioxide. After stirring for two hours the mixture was acidified with concentrated hydrochloric acid. The product was extracted into ether and the combined extracts washed with water until the washings were neutral to Congo-red indicator. The ether extracts were dried ($Na_2SO_4$) and the ether removed by distillation. The solid residue was crystallised from n-hexane. The acid product has mp 51° C.

Step B3: The production of trans-4-n-propylcyclohexylmethyl 4'-(4''-bromobiphenylyl) ketone A solution of trans-4-n-propylcyclohexylacetyl chloride (0.015 mole) [prepared from the acid with an excess of thionyl chloride] and 4-bromobiphenyl (0.014 mole) in dichloromethane (60 ml) was added dropwise to a suspension of aluminium trichloride (0.023 mole) in dichloromethane (20 ml), cooled in an ice bath. The reaction mixture was stirred during 18 hours and then poured onto a 20% v/v hydrochloric acid, ice/water mixture (200 ml) and stirred for 0.5 hours.

The aqueous mixture was shaken with chloroform (3×80 ml) and the combined chloroform extracts were washed with water and dried over anhydrous sodium sulphate. The solvent was removed by distillation and the residue crystallised from ethanol/toluene to give mp 150° C. Step C3: The production of 1-[trans-4'-n-propylcyclohexyl]-2-{4''-[4'''-bromobiphenylyl]} ethane A solution of the ketone prepared in Step B3 above in chloroform (70 ml) was added dropwise to a suspension of lithium aluminium hydride (0.03 mole) and aluminium trichloride (0.04 mole) in sodium dried ether (70 ml).

The mixture was then heated and stirred under reflux for 18 hours. The excess of lithium aluminium hydride was destroyed by the cautious addition of water and the mixture then poured into a 20% v/v mixture of hydrochloric acid and water and stirred for 1 hour.

The product was extracted into chloroform and the combined extracts washed with water, dried ($Na_2SO_4$), and the solvent removed by distillation. The residual solid was crystallised from ethanol/toluene. The product had the constants: C-N, 128° C.; N-I, 162° C.

Step D3: The production of 1-[trans-4'-n-propylcyclohexyl]-2-{4''-[4'''-cyanobiphenylyl]} ethane This is prepared in an analogous manner to Step G1 of Example 1.

The constants for this compound and others prepared similarly are given in Table 2 below.

TABLE 2

R—⟨H⟩—$CH_2 \cdot CH_2$—⟨○⟩—⟨○⟩—CN

| R | C–$S_A$/N (°C.) | $S_A$–N (°C.) | N–I (°C.) | ΔH k cal mol$^{-1}$ |
|---|---|---|---|---|
| n-$C_3H_7$ | 77.2 | — | 193.8 | 5.5 |
| n-$C_4H_9$ | 71.8 | 74.5 | 182.2 | — |

EXAMPLE 4

This example describes the preparation of 4-[trans-4'-n-alkylcyclohexylmethoxy]benzonitriles by the following route:

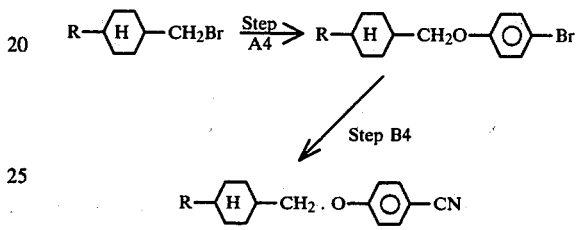

where R is a normal or branched alkyl group which may be chiral.

The synthetic steps where R=n-propyl will now be described by way of example.

Step A4: The production of 4-[trans-4'-n-propylcyclohexylmethoxy]bromobenzene.

Commercially available 4-bromophenol (0.04 mole), potassium carbonate (0.20 mole) and trans-4-n-propylcyclohexylmethyl bromide (0.04 mole) prepared in Step E1 of Example 1 were added to butan-2-one (120 ml). The mixture was stirred and heated under reflux for 48 hours.

On cooling, the mixture was poured into water (400 ml) and the solution shaken with ether (3×100 ml). The combined ether extracts were washed with water (2×100 ml) and dried over $MgSO_4$. The ether was removed by distillation and the residue crystallized from ethanol to give a product with mp 57.6° C.

Step B4: The production of 4-[trans-4'-n-propylcyclohexylmethoxy]benzonitrile.

This was prepared in an analogous manner to Step G1 of Example 1.

Physical constants for this compound and others similarly prepared are given in Table 3 below.

TABLE 3

R—⟨H⟩—$CH_2O$—⟨○⟩—CN

| R | C–N/I (°C.) | N–I (°C.) | ΔH k cal mol$^{-1}$ |
|---|---|---|---|
| n-$C_3H_7$ | 61.6 | (36.3) | 8.0 |
| n-$C_4H_9$ | 70.0 | (36.0) | 6.7 |
| n-$C_5H_{11}$ | 74.3 | (48.6) | 5.6 |
| n-$C_7H_{15}$ | 48.0 | 53.5 | 9.6 |
| n-$C_6H_{13}$ | 56.0 | 45.0 | — |

EXAMPLE 5

This example describes the preparation of 1-[trans-4'-alkylcyclohexyl]-2-[4''-cyanophenyl]ethanes by the following route:

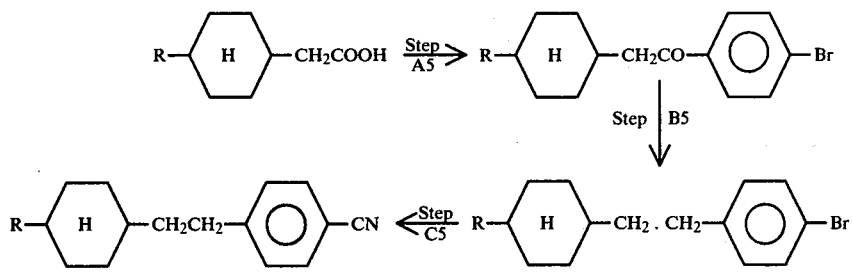

These compounds were prepared in an analogous manner to those described in Steps B3, C3 and D3 of Example 3.

Specific product examples are where R=n—$C_4H_9$, n—$C_5H_{11}$ and n—$C_6H_{13}$.

EXAMPLE 6

This example describes the preparation of 2-[trans-4'-alkylcyclohexylmethoxy]-6-cyanonapthalenes by the following route:

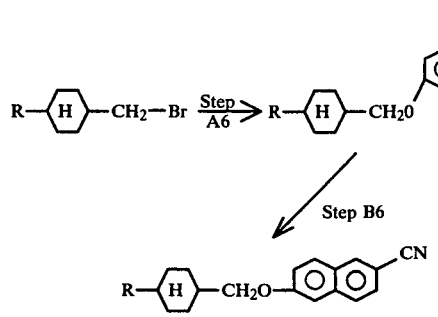

where R is a normal or branched alkyl group which may be chiral.

The synthetic steps where R is n-propyl will now be described by way of example.

Step A6: The production of 2-[trans-4'-n-propylcyclohexylmethoxy]-6-bromonapthalene.

This was prepared as in Step A4 of Example 4 but using commercially available 2-bromo-6-hydroxynapthalene.

The product had mp 113° C.

Step B6: The production of 2-[trans-4-n-propylcyclohexylmethoxy]-6-cyanonapthalene.

This was prepared in an analogous manner to Step G1 of Example 1.

Physical constants for this compound and others similarly prepared are given in Table 4 below.

TABLE 4

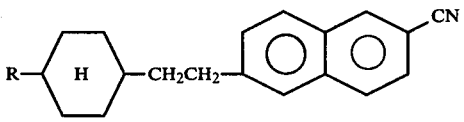

| R | C—N (°C.) | N—I (°C.) | ΔH k cal mol$^{-1}$ |
|---|---|---|---|
| n-$C_3H_7$ | 91.0 | 112.0 | 6.1 |
| n-$C_4H_9$ | 82.4 | 109.5 | 7.6 |
| n-$C_5H_{11}$ | 87.3 | 114.5 | 6.0 |
| n-$C_6H_{13}$ | 81.0 | 110.0 | 9.4 |
| n-$C_7H_{15}$ | 88.0 | 108.5 | 8.4 |

The data in Tables 1–4 show that none of the pure materials listed exhibits a liquid crystal phase at a low enough temperature to be of direct interest for commercial application. However, the compounds are of interest and use in this connection when used as eutectic mixtures with one another or with other liquid crystal forming materials.

EXAMPLE 7

Compounds of the form;

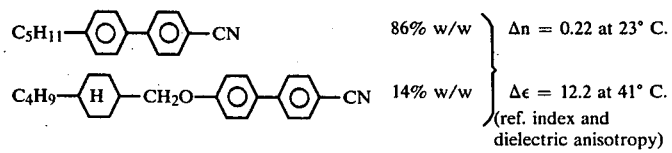

These are prepared by a method analogous to that of Example 3.

Specific product examples are where R=n—$C_3H_7$, n—$C_4H_9$, n—$C_5H_{11}$ and n—$C_6H_{13}$.

The following mixtures are examples and demonstrate the usefulness of the compounds described.

MIXTURE 1

C$_5$H$_{11}$—◯—◯—CN    86% w/w    Δn = 0.22 at 23° C.

C$_4$H$_9$—⟨H⟩—CH$_2$O—◯—◯—CN    14% w/w    Δε = 12.2 at 41° C.
(ref. index and dielectric anisotropy)

Transition temperatures    C—N - 11° C.

MIXTURE 2

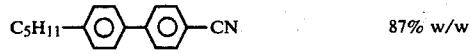 87% w/w

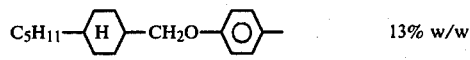 13% w/w

Transition temperatures: C—N, 14.5° C.
N—I, 35.3° C.

Other physical properties:
Viscosity: 34.8 cst at 20° C.
Dielectric anisotropy (ΔΣ): 13.13 at 1 kHz.

MIXTURE 3

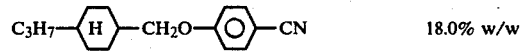 18.0% w/w

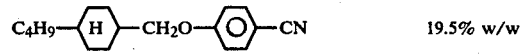 19.5% w/w

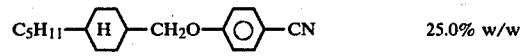 25.0% w/w

 29.5% w/w

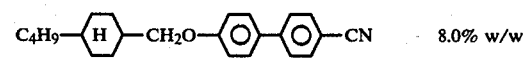 8.0% w/w

Transition temperatures: C—N, 10–15° C.
N—I, 54.5° C.

Other physical properties:
Dielectric anisotropy (ΔΣ): 6.4 at 1 kHz.

MIXTURE 4

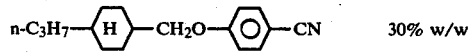 30% w/w

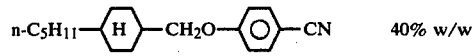 40% w/w

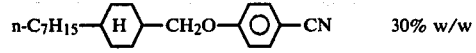 30% w/w

C—N* = 10–18° C., N—I = 45° C.

*This is the melting point of a metastable solid which forms on cooling quickly to −30° C. However, after some time the mixture segregates and the components melt/redissolve completely on heating to 50° C.: birefringence (Δn) = 0.11 at 25° C. dielectric anisotropy (Δε) = 10.9 at 29° C. Threshold voltage in polyvinyl alcohol aligned twisted nematic cell = 1.5 volts (rms) at 100 Hz.

MIXTURE 4

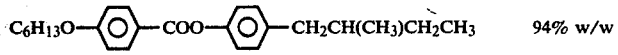 94% w/w

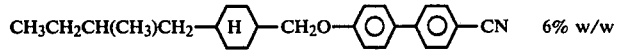 6% w/w

Transition temperatures: S_A—Ch, 27.3° C.
Ch—I, 43° C.

The following indicates the colour of light selectively reflected by this mixture (in the Grandjean state) with varying temperature.

| Selective Reflection | Temperature (°C.) |
|---|---|
| Red | 27.3 |
| Yellow | 27.8 |
| Green | 27.9 |
| Turquoise | 28.7 |
| Blue | 29.5 |
| Isotropic liquid | 43° C. |

The compounds of formula (I) above may be added to any one or more other compounds of the following known classes to form mixed liquid crystal systems:

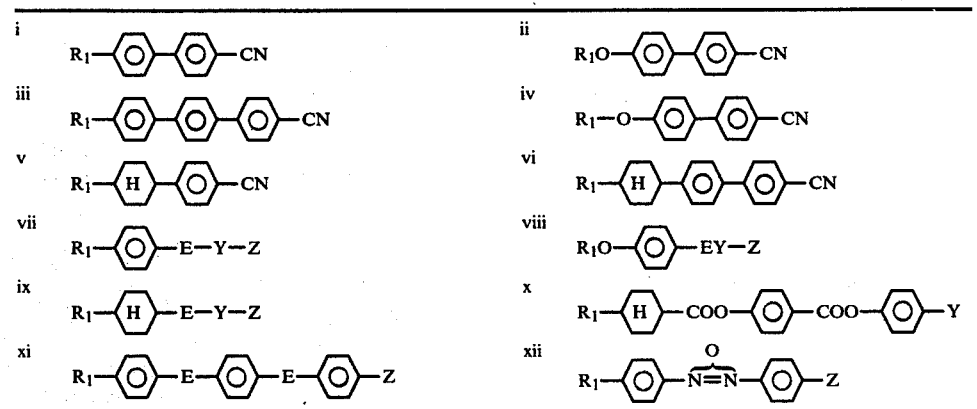

xiii 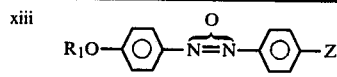

xiv 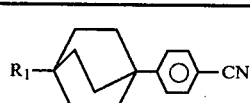

xv 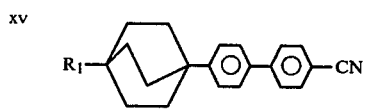

xvi 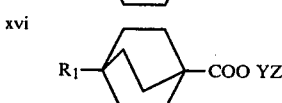

xvii 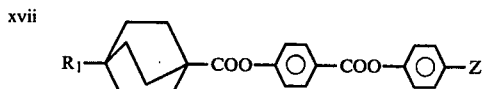

xviii 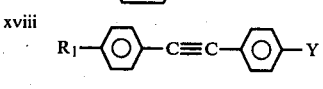

xxi 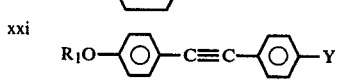

where $R_1$=alkyl (straight chain, branched or chiral),

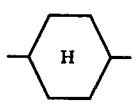

is a cyclohexane ring,

is a 2,2,2 bicyclo-octane ring, E is an ester linkage group CO.O or O.OC, Y is

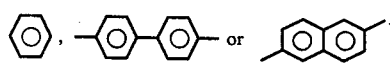

and Z is $R_1$, $OR_1$ or CN, or derivatives of these compounds containing a lateral substituent, eg methyl or halogen, on one of the benzene rings of the compound's molecular structure.

In this specification the term 'liquid crystal compound' is intended to include not only compounds which normally exhibit a liquid crystal phase; but also compounds which do not normally exhibit a liquid crystal phase but which nevertheless usefully affect some aspect of liquid crystal behaviour when dissolved in other liquid crystal compounds, eg by forming liquid crystal mixtures with mesophases having extended temperature ranges.

The construction of electro-optic display devices in which materials of the present invention may be incorporated for use is well known. For example such devices comprise dielectric transparent substrates having electrodes on their inner surfaces, a film of the liquid crystal material being sandwiched between the substrates.

I claim:

1. A liquid crystal compound having the formula:

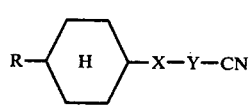

where R is an alkyl group containing up to 15 carbon atoms X is —CH$_2$.CH$_2$— or —CH$_2$O— and Y is

2. A liquid crystal compound as claimed in claim 1 and wherein R is an n-alkyl group containing from three to nine carbon atoms inclusive.

3. A liquid crystal compound as claimed in claim 1 and wherein R is a chiral branched alkyl group containing nine or less carbon atoms.

4. A liquid crystal compound as claimed in claim 2 and wherein X is —CH$_2$.CH$_2$— and Y is

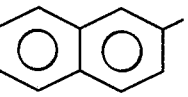

5. A liquid crystal compound as claimed in claim 1 and wherein X is —CH$_2$.CH$_2$— and Y is

6. A liquid crystal compound as claimed in claim 1 and wherein X is —CH$_2$.CH$_2$— and Y is

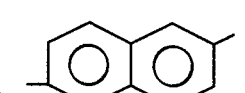

7. A liquid crystal compound as claimed in claim 1 and wherein X is —CH$_2$.O— and Y is 8. A liquid crystal compound as claimed in claim 1 and wherein X is —CH₂.O— and Y is

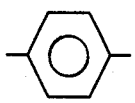

9. A liquid crystal compound as claimed in claim 1 and wherein X is —CH₂.O— and Y is

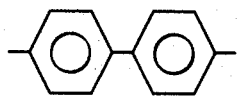

10. The liquid crystal compound

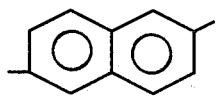

11. The liquid crystal compound

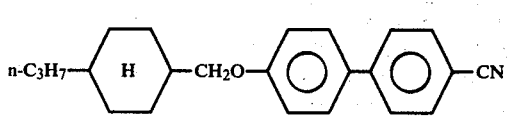

12. The liquid crystal compound

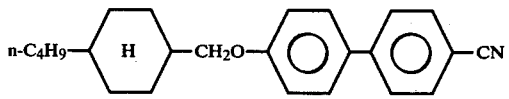

13. The liquid crystal compound

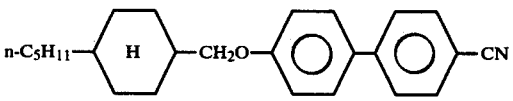

14. The liquid crystal compound

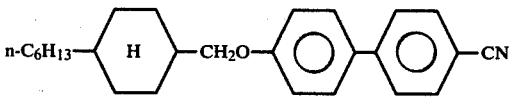

15. The liquid crystal compound

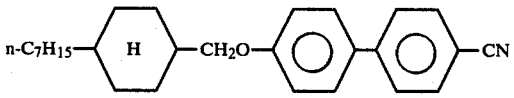

16. The liquid crystal compound

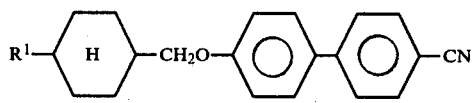

where R′ is (+) 2-methylbutyl.

17. The liquid crystal compound

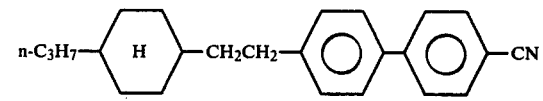

18. The liquid crystal compound

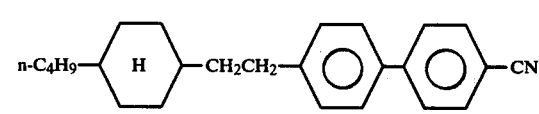

19. The liquid crystal compound

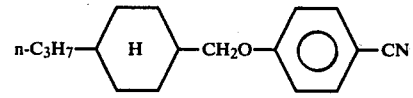

20. The liquid crystal compound

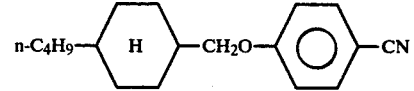

21. The liquid crystal compound

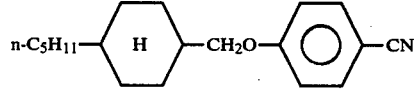

22. The liquid crystal compound

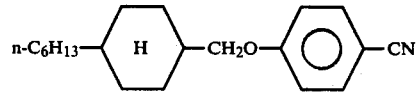

23. The liquid crystal compound

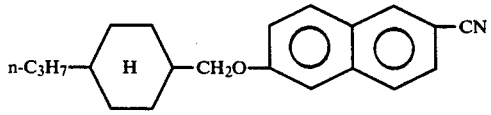

24. The liquid crystal compound

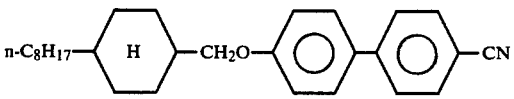

25. The liquid crystal compound

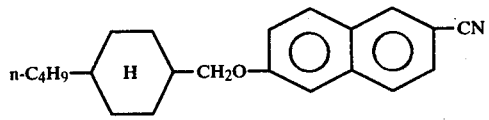

26. The liquid crystal compound

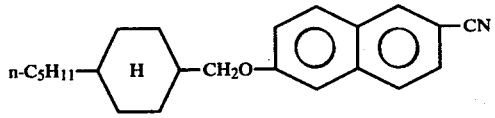

27. The liquid crystal compound

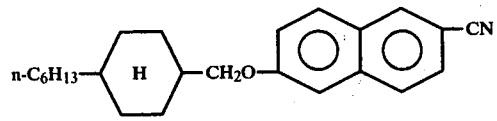

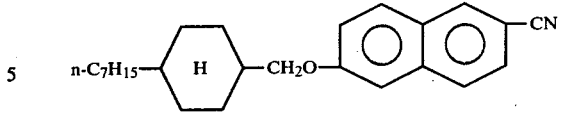

28. The liquid crystal material of claim 1 having a high positive dielectric anistropy and comprising at least two liquid crystal compounds of which one is a compound of the formula of claim 1.

29. The liquid crystal material of claim 28, comprising a cyanobiphenyl having the formula

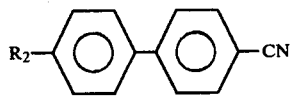

where $R_2$ is an n-alkyl group.

30. In a liquid crystal device including means for containing a region of liquid crystal material, a region of liquid crystal material contained in said containing means, and means for applying an external stimulus to the material to alter the molecular arrangement in the material, the improvement which comprises using as the liquid crystal material, a compound having the formula of claim 1, wherein the containing means includes two adjacent plates at least one of which is optically transparent, the liquid crystal material being contained in the space between the plates, said means for applying an electric field comprising a film of conducting material carrying an electrode deposited on the inner face surface of the plates.

* * * * *